(12) United States Patent
Mogenet et al.

(10) Patent No.: US 8,696,297 B2
(45) Date of Patent: Apr. 15, 2014

(54) METHOD AND SYSTEM FOR STABILIZING AN EGG TRAY

(75) Inventors: Laurent Mogenet, Libourne (FR); Jean-Claude Yvin, Plougoulm (FR); Christophe Dupont, Le Folgoet (FR)

(73) Assignee: Egg Chick Automated Technologies, Pace (FR)

( * ) Notice: Subject to any disclaimer, the term of this patent is extended or adjusted under 35 U.S.C. 154(b) by 558 days.

(21) Appl. No.: 12/527,541

(22) PCT Filed: Feb. 18, 2008

(86) PCT No.: PCT/FR2008/050259
§ 371 (c)(1),
(2), (4) Date: May 4, 2010

(87) PCT Pub. No.: WO2008/110729
PCT Pub. Date: Sep. 18, 2008

(65) Prior Publication Data
US 2010/0221093 A1  Sep. 2, 2010

(30) Foreign Application Priority Data

Feb. 16, 2007  (FR) ..................... 07 53312

(51) Int. Cl.
*B65G 1/133* (2006.01)
(52) U.S. Cl.
USPC ......................................... 414/752.1; 356/52
(58) Field of Classification Search
USPC ........... 901/30, 40; 414/403, 404, 589, 749.1, 414/749.5, 751.1, 752.1; 356/52, 55
See application file for complete search history.

(56) References Cited

U.S. PATENT DOCUMENTS

| 4,469,047 A | 9/1984 | Miller |
| 4,681,063 A | 7/1987 | Hebrank |
| 4,768,919 A * | 9/1988 | Borgman et al. ............... 53/495 |

(Continued)

FOREIGN PATENT DOCUMENTS

| EP | 1302102 | 4/2003 |
| EP | 1557083 | 7/2005 |

(Continued)

OTHER PUBLICATIONS

International Search Report for International Application No. PCT/EP2008/001046 dated Mar. 26, 2008.

(Continued)

*Primary Examiner* — Saul Rodriguez
*Assistant Examiner* — Glenn Myers
(74) *Attorney, Agent, or Firm* — Patterson Thuente Pedersen, P.A.

(57) ABSTRACT

The invention relates to an automated method for positioning eggs on a tray that comprises the automated detection of the presence/absence of eggs in the cells of a tray, and the picking-up of eggs from a supply and the placement thereof in the empty cells of a tray. The invention also relates to a system or positioning eggs on a stabilizing tray, the tray including evenly distributed cells in which the eggs are placed, one or more cells being likely not to contain eggs, this information being stored in an information processing unit, wherein said system includes a means in the form of a robot having an egg pick-up head that are driven by the information processing unit in order to pick up eggs from a supply tray and to place them in the empty cells of the stabilizing tray.

6 Claims, 1 Drawing Sheet

(56) References Cited

U.S. PATENT DOCUMENTS

| | | | |
|---|---|---|---|
| 4,805,778 A | | 2/1989 | Nambu |
| 4,903,635 A | | 2/1990 | Hebrank |
| 4,980,971 A | * | 1/1991 | Bartschat et al. ............... 29/833 |
| 5,136,979 A | | 8/1992 | Paul et al. |
| 5,207,311 A | * | 5/1993 | Terai .......................... 198/419.1 |
| 5,895,192 A | * | 4/1999 | Parnell et al. ............ 414/225.01 |
| 5,898,488 A | * | 4/1999 | Kuhl .............................. 356/53 |
| 5,941,696 A | | 8/1999 | Fenstermacher et al. |
| 6,286,455 B1 | | 9/2001 | Williams |
| 6,338,673 B2 | * | 1/2002 | Berry et al. ..................... 452/58 |
| 6,499,428 B1 | | 12/2002 | Prindle |
| 6,535,277 B2 | * | 3/2003 | Chalker et al. ................. 356/53 |
| 2003/0150387 A1 | | 8/2003 | Hebrank |
| 2004/0065263 A1 | | 4/2004 | Hebrank et al. |
| 2005/0030521 A1 | * | 2/2005 | Phelps et al. ................... 356/53 |
| 2005/0132964 A1 | | 6/2005 | Breuil et al. |
| 2005/0284376 A1 | | 12/2005 | Smith |
| 2006/0082759 A1 | | 4/2006 | Hebrank |
| 2006/0185601 A1 | | 8/2006 | Correa et al. |
| 2007/0044721 A1 | | 3/2007 | Ilich |
| 2010/0139567 A1 | | 6/2010 | Yvin et al. |
| 2010/0180821 A1 | | 7/2010 | Poulard et al. |
| 2010/0307419 A1 | | 12/2010 | Nadreau et al. |
| 2012/0017835 A1 | | 1/2012 | Nadreau et al. |

FOREIGN PATENT DOCUMENTS

| | | |
|---|---|---|
| EP | 1310164 | 3/2006 |
| FR | 2 858 919 A1 | 2/2005 |
| FR | 2 873 894 A1 | 2/2006 |
| JP | 63-107940 | 5/1988 |
| WO | WO98/31216 | 7/1998 |
| WO | WO 2006/078499 A2 | 7/2006 |

OTHER PUBLICATIONS

International Preliminary Report on Patentability and Written Opinion dated May 4, 2010 from International Application No. PCT/EP2008/063997.

International Preliminary Report on Patentability and Written Opinion dated Mar. 2, 2010 from International Application No. PCT/EP2008/061250.

Application and File History for U.S. Appl. No. 12/527,536, filed Dec. 15, 2009, inventor Yvin.

Application and File History for U.S. Appl. No. 12/740,649, filed Apr. 29, 2010, inventors Nadreau et al.

Application and File History for U.S. Appl. No. 12/675,946, filed Mar. 1, 2010, inventors Nadreau et al.

* cited by examiner

METHOD AND SYSTEM FOR STABILIZING AN EGG TRAY

PRIORITY CLAIM

The present application is a National Phase entry of PCT Application No. PCT/FR2008/050259, filed Feb. 18, 2008, which claims priority from French Application No. 0753312, filed Feb. 16, 2007, the disclosures of which are hereby incorporated by reference herein in their entirety.

FIELD OF THE INVENTION

The present invention relates to a method and an automated system for stabilizing egg trays.

BACKGROUND OF THE INVENTION

In the poultry industry, it is accepted that 5 to 30% of eggs are not fertile or viable, which leads to the absence of hatching of a chicken. To overcome this problem, some techniques have been developed for discriminating, for the purpose of elimination, between fertilized (having an embryo) and non-fertilized eggs. A currently known technical solution for discriminating between fertilized eggs is based on the use of optics or various luminous sources particularly laser as described in FR0512998.

This egg discriminating step is commonly called "egg candling." The elimination step of eggs identified as being non fertilized following the "candling" step is commonly called "removal" of eggs.

The combination of the "candling" and "removal" steps of eggs makes it possible to obtain a homogenous population of fertilized eggs likely to hatch into a chicken.

Techniques in embryology have made it possible to add various compounds beneficial to the chickens inside eggs, directly in the embryo or in the vicinity of the embryo. In particular, such beneficial compounds may result in improved growth of the chicken, such as by the prevention of illness, an increase in the percentage of hatched eggs, or even the improvement of the poultry's physical characteristics. The addition of compounds in the fertilized egg is commonly called in ovo treatment.

In the particular case of illness prevention, and more particularly in the case of vaccination, the in ovo treatment techniques based on the injection of the vaccine through the egg shell by needle are widely used. An injection system making the in ovo treatment possible while reducing the effect on embryos caused by the injection of the vaccine is described in patent FR1505870.

For economic reasons and in order to prevent any contamination risk linked to the treatment of the non fertilized eggs (there may be a risk of explosion or contamination due to the albumin contained in these eggs), it is preferable to carry out the in ovo treatment of fertilized eggs that are selected by a candling and removal step.

The economic viability of in ovo treatment mainly resides in the automation of the set of candling, removal and the actual treatment steps. Technical solutions of integration and automation of these steps have been described in patent FR2873894.

The currently available set of automated solutions for the candling and removal of eggs can lead to the random distribution of fertilized eggs spread out over an entire presentation tray. As a result, particularly complex and costly injectors for carrying out the in ovo treatment have been developed such as is described in WO06/078499.

Manual replacement of eggs on the presentation tray has also been utilized. In accordance with this technique, one or several operators may place eggs into the holes of the trays from which non fertilized eggs have been removed. This replacement step is commonly called "stabilizing."

Manual "stabilizing," however, may not be compatible with the processing rates which have been achieved through the automation of the "candling," and "removal" steps.

SUMMARY OF THE INVENTION

A system and method for stabilizing an egg tray according to the present invention substantially meets the aforementioned needs of the industry.

In an embodiment, the present invention relates to a method and a system that makes it possible to automatically replace the removed eggs after "candling" and "removal" steps in order to obtain trays of fertilized eggs distributed homogenously.

Thus, a purpose of the invention is an automated method for positioning eggs on a tray, comprising, in a automated fashion, the detection of the presence or absence of eggs in the cells of a tray, the picking up of eggs from a supply tray, and the placement of eggs in the empty cells of the tray.

According to an embodiment of the present invention, with an egg pick-up head, the eggs are picked up by groups from a supply tray or stabilizing tray comprising a number of egg cells that is a multiple of a group.

According to an embodiment of the present invention, all the eggs of a group are placed before picking up another group of eggs from the supply tray.

According to an embodiment of the present invention, the eggs are placed one at a time, or by groups of plural eggs, by moving the egg pick-up head in an X and Y directions above the tray to complete or stabilise.

Other features of the method will appear from the following description of an egg positioning system.

Thus, a purpose of the invention is also to provide a system for positioning eggs on a tray to be filled, the tray comprising evenly distributed cells in which eggs are positionned, one or more cells being likely not to contain eggs, this information being stored in an information processing unit, which system comprising means in the form of a robot having an egg pick-up head, driven by the information processing unit in order to pick up one or more eggs from a supply tray and to place them in empty cells of the tray to be filled.

According to an embodiment of the present invention, the system comprises a conveyor for moving the tray, under means for detecting the presence/absence of eggs in the cells of the tray, to the stabilizing station.

According to an embodiment of the present invention, the detection means are in the form of a gantry fitted with sensors placed over a conveyor and whereunder the tray moves.

According to an embodiment of the present invention, the egg pick-up head of the means in the form of a robot comprises pick-up means for picking-up a group of several eggs.

According to an embodiment of the present invention, the means in the form of a robot are arranged so as to be able to place the eggs in the cells of the stabilizing tray to be filled one by one or by group of plural eggs.

According to an embodiment of the present invention, the means in the form of a robot are arranged so as to be able to pick up the eggs by group from a supply tray, each group corresponding to a sub-multiple of the supply tray; the pick-up management makes it possible to successively pick up and in groups all the eggs placed in the supply tray.

According to an embodiment of the present invention, the means in the form of a robot comprise means for moving the pick-up head in X and Y directions in the stabilizing station.

According to an embodiment of the present invention, the system comprises a second conveyor for moving the supply tray, under second means for detecting the presence/absence of eggs in the cells of the tray, to the stabilizing station.

According to an embodiment of the present invention, these second detection means are shaped in the form of a gantry fitted with sensors placed over a conveyor and whereunder the supply tray moves.

According to an embodiment of the present invention, the stabilizing station is sized so as to make it possible for the means in the form of a robot to reach all the cells of the tray to be filled and to place an egg thereto, whatever the position of the egg at the picking-up means is.

According to an embodiment of the present invention, the picking-up means are operable by one or several, being controlled by the information processing unit; the latter is able to manage the deposition of several eggs simultaneously according to the empty cells placed in the operating range of the picking up means according to the positioning of the robot-forming means, by taking into account the available eggs carried by these means.

BRIEF DESCRIPTION OF THE DRAWINGS

The invention will be better understood upon reading the following description of various embodiments of the present invention, given by way of example and made with reference to the accompanying drawings, wherein.

Figure 1:
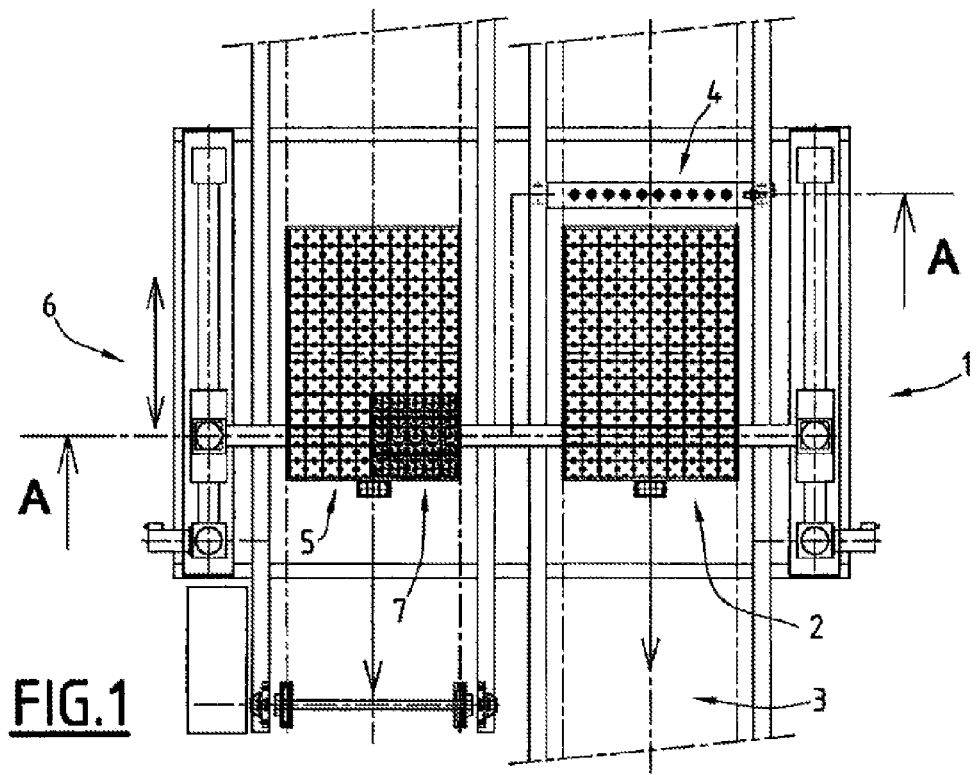
FIG. 1 is a top view of a stabilizing system according to an embodiment of the present the invention.
Figure 2:
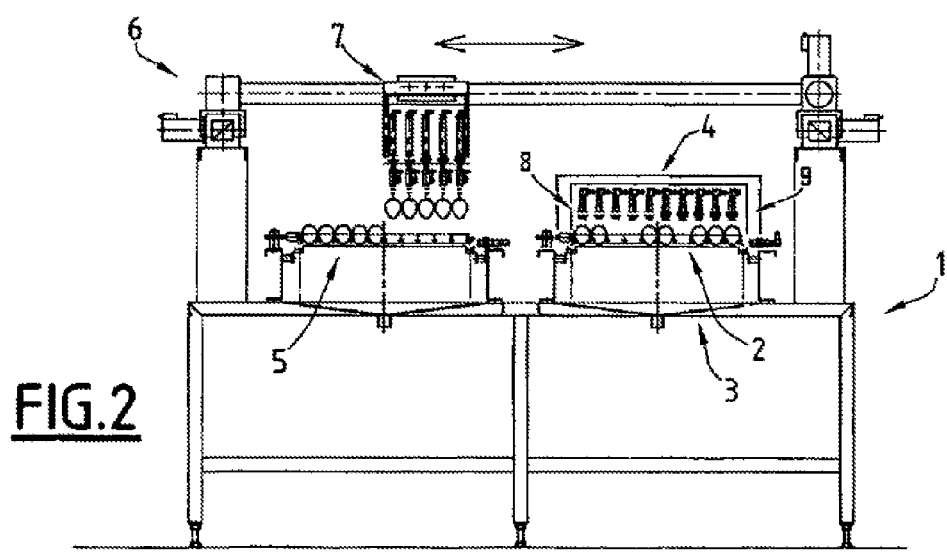
FIG. 2 is a cross-sectional view, taken according to line A-A of FIG. 1.

While the present invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

On these figures has been illustrated a stabilizing system designated by the general reference 1 of egg trays, whereof one is designated by the general reference 2, to be moved on a conveyor or on any other transport means designated by the general reference 3 and exhibiting any appropriate structure.

In fact, such a system may be integrated into a classic-type egg-processing machine as has previously been indicated.

On its entry in the stabilizing system, the egg tray passes under a gantry designated by the general reference 4 on these figures, fitted with means for detecting 8 the presence or absence of an egg in each cell of the tray.

Various means for implementing these detection means 8 may be contemplated, be they optical or not.

The detection is thus servocontrolled classically at the displacement speed of the tray to obtain a complete and precise analysis of the tray in its entirety and of each of its cells, in order to determine the presence or absence of an egg in each cell of the tray.

Alternatively, this detection device 9 may be omitted, and the information relating to the presence or absence of eggs may come from a prior candling and removal operation. However, it is advantageous to provide this detection device 9 as it makes it possible to eliminate the risk of non-removal of the eggs due to a failure during this prior step.

Once the tray has been fully analyzed, this stabilizing tray to be filled 2 arrives into a stabilizing station wherein automated means in the form of a robot are adapted to pick up replacement eggs from a stabilizing tray or a supply tray designated by the general reference 5 on these figures, and to stock-up, i.e., fill, the empty holes of the tray to be filled.

To this end, the system comprises means in the form of a robot designated by the general reference 6 on these figures, comprising means for moving an egg pick-up head, designated by the general reference 7 on these figures, in an X and Y directions, this pick-up head comprising means for picking up groups of eggs in the stabilizing tray 5 to arrange them in the empty cells of the tray to be filled 2. The stabilizing tray 5 comprises a number of cells that is a multiple of the number of eggs of the picked-up group.

These means in the form of a robot are thus driven by a computer or information processing unit, also connected to the detection means 8 of gantry 4 for locating the empty place(s) of the tray to be filled 2. The means are also driven to search successively the groups of eggs in the stabilizing tray 5.

In the embodiment described in these figures, the pick-up head comprises picking up means of a group of twenty five eggs distributed over five rows of five columns and the stabilizing tray corresponds to six groups of twenty five eggs.

Needless to say that various embodiments may be contemplated.

For example, the means 6 in the form of a robot may be actuated by electric motors or other.

The pick-up head 7 and the egg picking up means may also exhibit any kind of appropriate structure provided with a jack for lifting/descending suction-cup means associated to suction means, whereof the structure is well known in the state of the art to handle eggs of this type.

Once the tray to be filled is full, it may then be brought towards another station of the processing machine, that is, for example a station for vaccine injection into these eggs.

Various modes for obtaining the stabilizing trays can be contemplated.

For example, they can be filled manually or obtained during the passage of a first tray under the detection means of the gantry 4.

It is also to be noted that the tray to be filled may stop or not in position in the stabilizing tray, for example, on the basis of the number of holes thereof to completed.

Thus, it is to be understood that such a system exhibits a number of advantages regarding the egg processing rate.

The invention claimed is:

1. A system for positioning a plurality of eggs post-candling, the system comprising:
   a tray to be filled including substantially evenly distributed cells for receiving at least a portion of the plurality of eggs, each cell characterized by a likelihood that the cell does not contain one of the plurality of eggs;
   an information processing unit for storing data for each cell indicative of the likelihood that the cell does not contain one of the plurality of eggs;
   robotic means for picking up at least one egg from a supply tray and placing the at least one egg in an at least one empty cell of the tray to be filled, the robotic means having an egg pick-up head and being driven by the information processing unit;
   a stabilizing position;

a conveyor for moving the tray to be filled to the stabilizing position;

wherein the system further comprises a post-candling detecting device adapted to detect a presence or an absence of one of the plurality of eggs in the cells of the tray to be filled, said conveyor moving the tray to be filled under the post-candling detecting device; and the post-candling detecting device comprising a gantry having sensors arranged over the conveyor such that the tray to be filled is movable under the sensors.

2. The system according of claim 1, wherein the egg pick-up head comprises means for picking up a two or more of the plurality of eggs.

3. The system of claim 2, wherein the robotic means is configured to place the at least a portion of the plurality of eggs individually or by groups into the cells of the tray to be filled.

4. The system according of claim 2, wherein the robotic means is configured to pick up a portion of the plurality of eggs by group from the supply tray, each group corresponding to a sub-multiple of the supply tray.

5. The system of claim 1, wherein the robotic means comprises means for moving the egg pick-up head in a first X direction and a second Y direction in a stabilizing station.

6. The system of claim 1, further comprising:
   a second means for detecting a presence or an absence of one of the plurality of eggs in the cells of the supply tray;
   a second conveyor for moving the supply tray under the second means for detecting to the stabilizing position.

\* \* \* \* \*